(12) United States Patent
Kwak et al.

(10) Patent No.: US 10,495,589 B2
(45) Date of Patent: Dec. 3, 2019

(54) DETERMINING PERMEABILITY OF POROUS MEDIA BASED ON NUCLEAR MAGNETIC RESONANCE MEASUREMENT

(71) Applicant: Saudi Arabian Oil Company, Dhahran (SA)

(72) Inventors: Hyung Tae Kwak, Dhahran (SA); Ahmad Mubarak Al-Harbi, Dammam (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 15/955,061

(22) Filed: Apr. 17, 2018

(65) Prior Publication Data
US 2019/0317034 A1    Oct. 17, 2019

(51) Int. Cl.
| | | |
|---|---|---|
| G01V 3/00 | (2006.01) |
| G01N 24/08 | (2006.01) |
| G01R 33/30 | (2006.01) |
| G01R 33/44 | (2006.01) |

(52) U.S. Cl.
CPC ........... *G01N 24/081* (2013.01); *G01R 33/30* (2013.01); *G01R 33/448* (2013.01)

(58) Field of Classification Search
CPC .................................................. G01N 24/081
USPC ................................................ 324/303, 306
See application file for complete search history.

(56) References Cited

U.S. PATENT DOCUMENTS

| | | |
|---|---|---|
| 5,289,124 A | 2/1994 | Jerosche-Herold et al. |
| 5,428,291 A | 6/1995 | Thomann et al. |
| 5,696,448 A | 10/1997 | Coates et al. |
| 7,221,158 B1 | 5/2007 | Ramakrishnan |
| 2005/0168220 A1 | 8/2005 | Lenormand et al. |
| 2010/0264915 A1* | 10/2010 | Saldungaray ........... E21B 43/16 324/303 |
| 2013/0325348 A1* | 12/2013 | Valori ....................... G01V 3/32 702/11 |

FOREIGN PATENT DOCUMENTS

| | | |
|---|---|---|
| EP | 2872741 | 5/2015 |
| EP | 2888612 | 7/2015 |

OTHER PUBLICATIONS

Ahmed et al., "Permeability Estimation: The Various Sources and Their Interrelationships," Journal of Petroleum Technology vol. 43 (5), SPE-19604-PA, May 1991, 10 pages.

(Continued)

*Primary Examiner* — Melissa J Koval
(74) *Attorney, Agent, or Firm* — Fish & Richardson P.C.

(57) ABSTRACT

The present disclosure describes methods and systems, including computer-implemented methods, computer program products, and computer systems, for determining a permeability of a rock sample. One method includes measuring a first set of Nuclear Magnetic Resonance (NMR) relaxation times for the rock sample saturated with regular water ($H_2O$); injecting heavy water ($D_2O$) into the rock sample; measuring a second set of NMR relaxation times for the rock sample after injecting $D_2O$; calculating a pore connectivity factor based on the first set of NMR relaxation times and the second set of NMR relaxation times; and calculating the permeability of the rock sample based on the pore connectivity factor.

8 Claims, 3 Drawing Sheets

(56) References Cited

OTHER PUBLICATIONS

Chen et al., "Pore-connectivity based permeability model for complex carbonate formations," presented at the SPWLA 49th Annual Logging Symposium, May 25-28, 2008, 11 pages.

Coates et al., "The MRIL in Conoco 33-1, An investigation of a new magnetic resonance imaging log," presented at the 32nd SPWLA Annual Logging Symposium, Jun. 16-18, 1991, 24 pages.

Kenyon, "Petrophysical principles of application of NMR logging," The Log Analyst vol. 38 (2), Mar.-Apr. 1997, 23 pages.

Schaefer et al., "Measurement of pore connectivity to describe diffusion through a nonaqueous phase in unsaturated soils," Journal of Contaminant Hydrology, vol. 40, Issue 3, Dec. 15, 1999, 18 pages.

Seevers, "A Nuclear Magnetic Method for Determining the Permeability of Sandstones," Paper L, presented at the SPWLA 7th Annual Logging Symposium, May 8-11, 1966, 14 pages.

Timur, "An investigation of permeability, porosity, and residual water saturation relationships for Sandstone Reservoirs," The Log Analyst vol. 9 (4), Jul.-Aug. 1968, 10 pages.

Timur, "Effective Porosity and Permeability of Sandstones Investigated Through Nuclear Magnetic Principles," The Log Analysis 10(1), presented at SPWLA Ninth Annual Logging Symposium, Jun. 23-26, 1968, 18 pages.

Timur, "Pulsated Nuclear Magnetic Resonance Studies of Porosity, Movable Fluid and Permeability of Sandstones," Journal of Petroleum Technology, vol. 21 (6), SPE-2045-PA, Jun. 1969, 12 pages.

International Search Report and Written Opinion issued in International Application No. PCT/US2019/024753 dated Jul. 23, 2019, 15 pages.

Chardaire-Riviere et al., "Principle and Potential of Nuclear Magnetic Resonance Applied to the Study of Fluids in Porous Media," Oil and Gas Science and Technology: Ruve De L'Institut Francais Du Petrole, Editions Technip, Paris, vol. 47, No. 4, Jul. 1992, 21 pages.

Thompson et al., "Deuterium magnetic resonance and permeability in porous media," Journal of Applied Physics, vol. 65, No. 8, Apr. 15, 1989, 6 pages.

\* cited by examiner

DETERMINING PERMEABILITY OF POROUS MEDIA BASED ON NUCLEAR MAGNETIC RESONANCE MEASUREMENT

TECHNICAL FIELD

This disclosure relates to exploration and production of hydrocarbons and, more specifically, to determining permeability of porous media using Nuclear Magnetic Resonance (NMR).

BACKGROUND

Rocks in a hydrocarbon reservoir store hydrocarbons (for example, petroleum, oil, gas, or any combinations thereof) by trapping the hydrocarbons within porous formations in the rocks. Permeability measures the ability of a fluid to flow through porous media such as reservoir rocks. The permeability of porous media is related to the porosity of porous media and to the quality of the porous media. Porosity is a measure of the void (empty) spaces in a material. Porosity is a fraction of the volume of voids over the total volume. Porosity is represented as a number between 0 and 1 or, as a percentage, between 0 and 100%. The quality of the porous media refers to the shapes of the pores in the porous media and their level of connectedness. The level of connectedness indicates whether the porous media is compartmentalized or networked. The compartmentalized porous media restricts the ability of a fluid to flow through it. The porous media that is networked through a matrix of connected pores may enable the fluid to flow through it. The permeability of a porous media sample taken from a reservoir indicates the ability of a hydrocarbon bearing formation to flow and produce hydrocarbon products in the reservoir.

SUMMARY

The present disclosure describes methods and systems, including computer-implemented methods, computer program products, and computer systems for determining permeability. One method for determining a permeability of a rock sample includes: measuring a first set of Nuclear Magnetic Resonance (NMR) relaxation times for the rock sample saturated with regular water (H$_2$O); injecting heavy water (D$_2$O) into the rock sample; measuring a second set of NMR relaxation times for the rock sample after injecting D$_2$O; calculating a pore connectivity factor based on the first set of NMR relaxation times and the second set of NMR relaxation times; and calculating the permeability of the rock sample based on the pore connectivity factor.

Other implementations of this aspect include corresponding computer systems, apparatuses, and computer programs recorded on one or more computer storage devices, each configured to perform the actions of the methods. A system of one or more computers can be configured to perform particular operations or actions by virtue of having software, firmware, hardware, or a combination of software, firmware, or hardware installed on the system that, in operation, cause the system to perform the actions. One or more computer programs can be configured to perform particular operations or actions by virtue of including instructions that, when executed by data processing apparatus, cause the apparatus to perform the actions.

The details of one or more implementations of the subject matter of this specification are set forth in the accompanying drawings and the subsequent description. Other features, aspects, and advantages of the subject matter will become apparent from the description, the drawings, and the claims.

DETAILED DESCRIPTION

The following description is presented to enable any person skilled in the art to make and use the disclosed subject matter, and is provided in the context of one or more particular implementations. Various modifications to the disclosed implementations will be readily apparent to those skilled in the art. The general principles defined in this disclosure may be applied to other implementations and applications without departing from scope of the disclosure. Thus, the present disclosure is not intended to be limited to the described or illustrated implementations, but is to be accorded the widest scope consistent with the principles and features disclosed in this disclosure.

This disclosure generally describes methods and systems, including computer-implemented methods, computer program products, and computer systems, for determining permeability of porous media. One technique to understand properties of the hydrocarbon reservoir is to develop computer-generated software models of all, or portions, of the reservoir. To develop such models, a reservoir rock sample from the hydrocarbon reservoir is evaluated and results of the evaluation are provided as an input to the computer software program that generates the software models. The reservoir rock sample can be evaluated by performing one or more of several experiments under laboratory conditions or under reservoir conditions. The reservoir conditions refer to the conditions experienced by the sample in the hydrocarbon reservoir.

Permeability is one of the parameters of the reservoir rock sample that can be evaluated. Permeability is an important parameter for reservoir evaluation and optimization. Permeability can be used to determine the potential productivity of producing a hydrocarbon reservoir. Permeability can also be used to optimize extraction of the stored hydrocarbons from the reservoir in various steps of a production operation, such as water flooding and enhanced oil recovery (EOR).

Permeability can be determined based on the fluid flow rate under a pressure gradient. Permeability studies are described in this disclosure in the context of reservoir rock samples, that is, rock samples that can be found in a hydrocarbon reservoir and that can trap hydrocarbons within their pore systems. The studies and the findings described in this disclosure can be applicable to any type of porous media, for example, porous media that include homogeneous pore systems (pore systems having pores of substantially same size) or inhomogeneous pore systems (pore systems having multiple pore sub-systems, each of different sizes). In some cases, the rock sample can also be referred to as a porous media sample.

In some implementations, permeability can be determined using nuclear magnetic resonance (NMR) measurements. In a NMR measurement, NMR relaxation time, for example T1 relaxation time and T2 relaxation time, can be measured. T1 relaxation time and T2 relaxation time can also be referred to as the longitudinal relaxation time and the transverse relaxation time, respectively. The NMR relaxation time can indicate the pore body sizes, and permeability can be calculated based on the pore body sizes using permeability models. Examples of permeability models include the Coates model and the geometric mean of relaxation time model. Because permeability is affected by pore throats instead of pore bodies, the accuracy of these permeability models depends on the correlation between pore body size and the pore throat size. For clastic samples, there is a strong correlation between the pore body size and the pore throat size. For carbonate rocks, the correlation between the sizes of pore body and pore throat varies, because carbonate rocks are originated from various depositional environment and post-depositional diagenetic processes. Thus, for porous media having a weak correlation between the size of pore body and throats, such as carbonate rocks, a pore connectivity factor is introduced as a correction factor to the permeability model.

Figure 6:
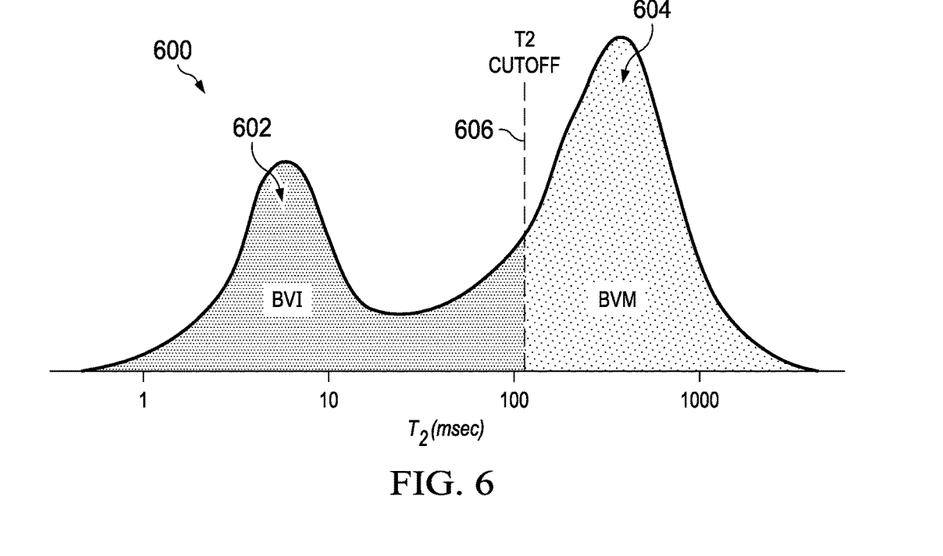
FIG. 6 is a schematic diagram illustrating an example determination of the values of bulk volume movable (BVM) and bulk volume irreducible (BVI), according to an implementation Like reference numbers and designations in the various drawings indicate like elements.

Equation (1), sometimes referred to as the Timur-Coats question, describes the Coats model as follows:

$$k = \left(\frac{\phi}{C}\right)^m \cdot \left(\frac{BVM}{BVI}\right)^n \qquad \text{Eq. (1)}$$

where k is permeability, $\phi$ is porosity, bulk volume movable (BVM) and bulk volume irreducible (BVI) represent the total volume of movable fluid and immovable fluid, respectively. FIG. 6 is a schematic diagram 600 illustrating an example determination of the values of BVM and BVI, according to an implementation. In FIG. 6, x-axis is NMR relaxation time T2 in units of microsecond (msec), and y-axis is fluid volume in units of milliliter (ml). As illustrated, the values of BVM and BVI, represented by the area 602 and 604 in FIG. 6, can be determined based on a cutoff value, represented as the T2 cutoff value 606. The fluid volume (area under NMR relaxation time T2 distribution) shorter than the T2 cutoff value is BVI. The fluid volume longer than the T2 cutoff value is BVM. In another example, BVI and BVM can also be determined based on the distribution of NMR relaxation time T1 and a T1 cutoff value. C is the lithologic constant. m is the porosity exponent. m is used as a weighting factor that account for the amount of porosity that contributes to flow. C and m can be empirically determined by laboratory studies on consolidated materials. In one example implementation, C is determined to be 10 and m is determined to be 4. n is the saturation exponent, which can be set to 2 based on the Archie equation.

Equation (2) describes the modified permeability model as follows:

$$k = \left(\frac{\phi}{C}\right)^m \cdot \left(\frac{p \cdot BVM}{BVI + (1-p) \cdot BVM}\right)^n \qquad \text{Eq. (2)}$$

In equation (2), p is the connectivity factor, where p takes the value between 0 and 1. When p=1, all pores are well connected to each other and Eq. (2) reduces to the original Timur-Coats equation (Eq. (1)).

In some cases, the pore connectivity factor can be obtained by using imaging technologies, such as micro- and nano X-ray computed tomography (CT) scan. However, these measurements are conducted for small size of sample, for example less than 1 mm in length. Therefore, the pore connectivity factor for a rock sample cannot be directly measured. Instead, upscaling may be used in combination with the imaging technologies. These techniques may be expensive and inaccurate.

In some cases, the pre connectivity factor can be determined based on single phase fluid displacement rate. The pore connectivity factor can be calculated from the fluid connectivity through different pore systems which can be derived by D$_2$O displacement rate for each pore system. In the context of Petrophysics, a pore system refers to an aggregate of pores and pore throats that share a similar morphology. A considerable portion of reservoir rocks have multiple pore systems. These pore systems can have different sizes and are inter-connected. The pore connectivity can be calculated by comparing the amount of D$_2$O displaced H$_2$O in each pore systems. FIGS. 1-6 provide additional details of these implementations.

Figure 1:
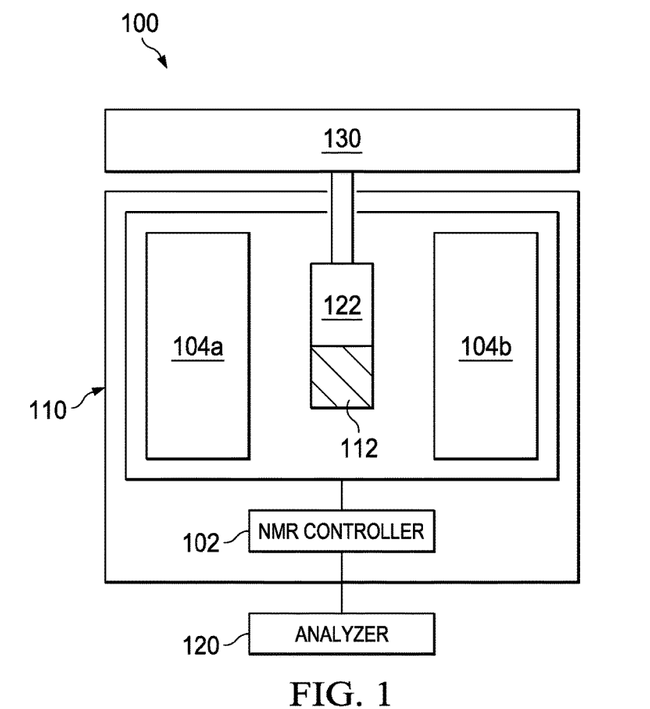
FIG. 1 is a schematic diagram of a system for determining a permeability of a reservoir rock sample based on the Nuclear Magnetic Resonance (NMR) relaxation times, according to an implementation.

FIG. 1 is a schematic diagram of a system 100 for determining a permeability of a reservoir rock sample based on the NMR relaxation times, according to an implementation. The system 100 includes an NMR instrument 110 connected to an analyzer 120 and a water pipe 130. The NMR instrument 110 represents an NMR instrument that is configured to measure NMR relaxation times. Examples of the NMR instrument include a low-field NMR instrument. In some implementations, the NMR instrument 110 can include a NMR controller 102 connected to one or more NMR magnets, for example, a first NMR magnet 104a or a second NMR magnet 104b, or both. In some cases, fluid redistribution during NMR measurements for a range of temperatures may cause the experimental errors, especially for the porous media samples with high permeability. For these types of samples, additional external magnets with high magnetic field can be used to shorten the NMR data acquisition time.

The NMR instrument 110 also includes a NMR sample cell 122. The NMR sample cell 122 is configured to sustain high pressure and high temperature (HPHT) conditions. For example, the NMR sample cell 122 can withstand up to 15,000 pounds per square inch (PSI) and up to 250 degrees Celsius (° C.) for samples of less than 5 millimeter (mm) in diameter or up to 5,000 PSI and up to 150° C. for samples of about 1.5 inch in diameter. A sample 112 is placed in the NMR sample cell 122 for measurement. The sample 112 can be any shape of porous media that can fit the NMR sample cell 122. For example, the sample 112 can be a rock core plug or a rock chip. The NMR controller 102 controls the NMR instrumentation. For example, the NMR controller 102 can provide instructions to the NMR instrumentation to measure the relaxation times at different temperatures. The NMR controller 102 can also receive the measurement results of relaxation times.

The system 100 also includes an analyzer 120. The analyzer 120 can implement computer software operations to determine a permeability of the sample 112 based on the measured relaxation times. In some implementations, the analyzer 120 and the NMR controller 102 can be implemented as different computing devices. Alternatively, the NMR controller 102 and the analyzer 120 can be implemented as a single entity.

The water pipe 130 provides circulating fluid to the NMR sample cell 122. The circulating fluid can be water, oil or other liquids. The water pipe 130 can include other components such as a pump, a gauge, a reservoir that can hold and inject the fluid, or any combinations thereof.

Figure 2:
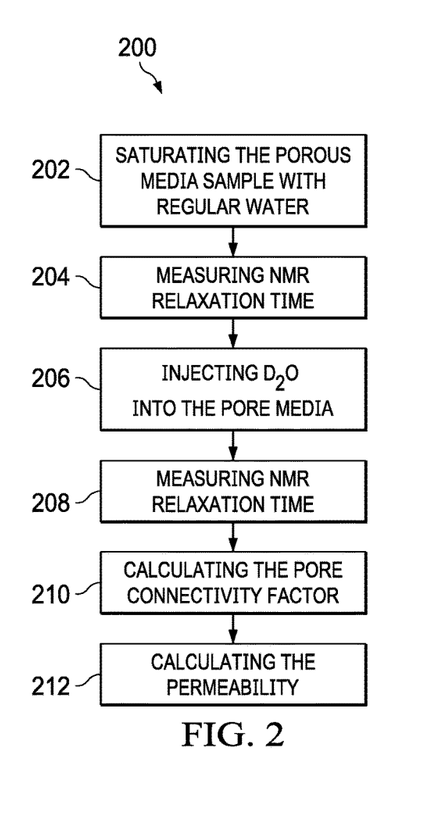
FIG. 2 is an example of a process for determining a permeability of a reservoir rock sample based on NMR relaxation times, according to an implementation.

FIG. 2 is an example of a process 200 for measuring permeability of a reservoir rock sample based on NMR relaxation times, according to an implementation. For clarity of presentation, the description that follows generally describes process 200 in the context of FIGS. 1 and 3-6. However, it will be understood that process 200 may be performed, for example, by any other suitable system, environment, software, and hardware, or a combination of systems, environments, software, and hardware, as appropriate. In some implementations, various steps of process 200 can be run in parallel, in combination, in loops, or in any order.

At 202, a porous media sample is saturated with regular water. The porous media sample can be collected from a reservoir. In one example, the porous media sample is a cylindrical rock core plug that is drilled from a rock sample collected at the reservoir. The porous media sample can have other shapes. The porous media sample can be saturated using core flooding. In this step, regular water ($H_2O$) is used for saturation.

At 204, the NMR relaxation time of the saturated pore media sample is measured. The NMR relaxation time can include the T1 relaxation time for the water-saturated sample, denoted as $T_{1,\,water}$, the T2 relaxation time for the water-saturated sample, denoted as $T_{2,\,water}$, or both.

At 206, heavy water ($D_2O$) is injected into the pore media sample. The injection continues until there is no more water displaced by $D_2O$. In some implementations, hydraulic pumps are used to inject the heavy water into the first pore system. $D_2O$ is chemically equivalent to regular water ($H_2O$), but is invisible for hydrogen the ($^1H$) NMR signal. Therefore, using heavy water isolates the NMR signal within the sample.

At 208, the NMR relaxation time of the pore media sample injected with $D_2O$ is measured. The NMR relaxation time can include the T1 relaxation time for heavy water-saturated sample, denoted as $T_{1,\,D2O}$, the T1 relaxation time for heavy water-saturated sample, denoted as $T_{2,\,first}$, or both.

At 210, the pore connectivity factor is calculated based on the measured NMR relaxation times. In one example, a pore media sample that has two pore systems. The pore connectivity factor of the pore media can be calculated based on the ratio of the volume displacements of the two pore systems, as shown in Equation (3):

$$p = \frac{V_1}{V_2} \quad (3)$$

where p represents the pore connectivity factor, $V_1$ represents the volume displacement of the first pore system, $V_2$ represents the volume displacement of the first pore system.

Because the pore connectivity factor takes the value between 0 and 1, the pore system having a smaller size is designated as the first pore system, while the pore system having a larger size is designated as the first pore system. The size of the pore system can be estimated based on a measurement of a diameter of the pore system. Thus, if the diameter of the first pore system is smaller than the diameter of the second pore system, the first pore system has a smaller size than the second pore system. In another example, the size of the pore system can be calculated based on images of the pore media sample.

Volume displacements for the first injection and the second injection can be calculated based on the NMR relaxation times measured at the step 208. In some cases, the volume displacement can be calculated based on the T1 relaxation times: $T_{1,\,water}$, $T_{1,\,D2O}$, and $T_{1,\,D2O}$. Alternatively, the volume displacement can be calculated based on the T2 relaxation times: $T_{2,water}$, $T_{2,D2O}$, and $T_{2,D2O}$. In some cases, both T1 relaxation time and T2 relaxation times can be used jointly in calculating the volume displacements.

Figure 3:
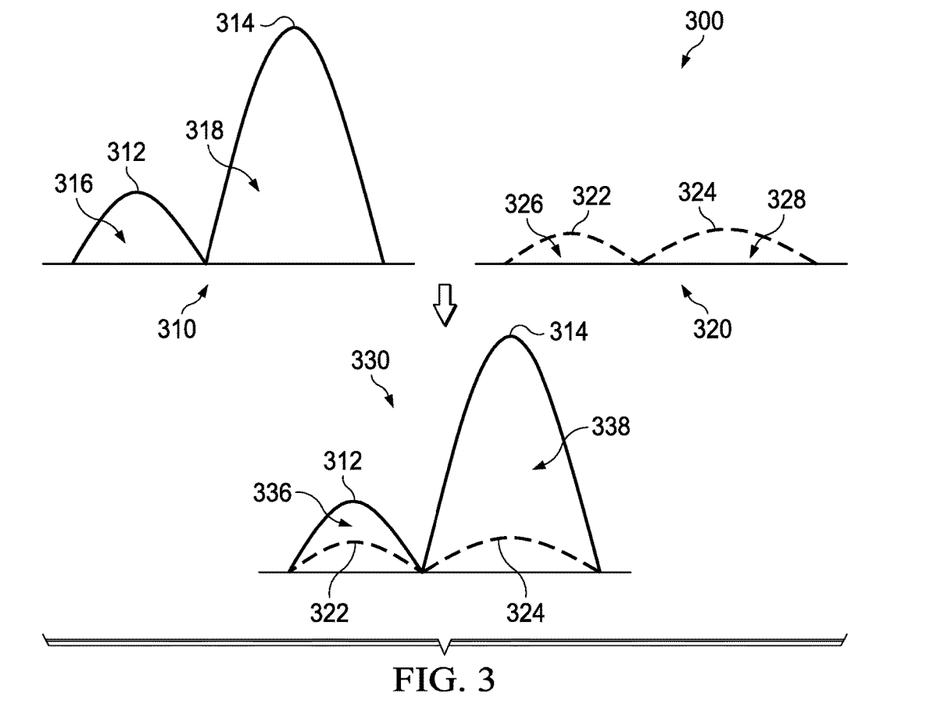
FIG. 3 is a schematic diagram illustrating a calculation of area changes based on NMR T1 relaxation time, according to an implementation.

FIG. 3 is a schematic diagram 300 illustrating a calculation of the volume displacement based on NMR T1 relaxation time, according to an implementation. The diagram 300 includes a chart 310 and a chart 320. The chart 310 illustrates the T1 relaxation time distribution for the sample after saturated by water. The chart 310 includes distribution curves 312 and 314, representing the T1 relaxation time distribution measured at the step 204 for the first pore system and the second pore system, respectively. In the charts 310 and 320, x-axis is NMR relaxation time (either T1 or T2) in units of msec, and y-axis is either fluid volume in units of ml or porosity in units of p.u. The chart 320 illustrates the T1 relaxation time distribution for the sample after injected by heavy water until the displacement ends. The chart 320 includes distribution curves 322 and 324, representing the T1 relaxation time distribution measured at the step 208 for the first pore system and the second pore system, respectively.

As illustrated, the chart 310 also includes areas 316 and 318 that are associated with the distribution curves 312 and 314, respectively. The sizes of the areas 316 and 318 can be calculated by taking an integral of the respective distribution curve. The areas 316 and 318 represents the volume of the first and the second pore system after saturated with water, respectively. Similarly, the chart 320 also includes areas 326 and 328 that are associated with the distribution curves 322 and 324, respectively. The areas 326 and 328 represents the volume of water saturated first and the second pore system after injected with heavy water, respectively.

The ratio between the volume displacements of the two pore systems, and therefore the pore connectivity factor, can be calculated based on the ratio of the area changes associated with the distribution curves. Equation (4) shows an example calculation of the pore connectivity factor p based on the ratio of area changes associated with the distribution curves:

$$p = \frac{(A_{1,water} - A_{1,D2O})/A_{1,water}}{(A_{2,water} - A_{2,D2O})/A_{2,water}} \quad \text{Eq. (4)}$$

where $A_{1,water}$ represents the size of the area 316, $A_{1,D2O}$ represents the size of the area 326, $A_{2,water}$ represents the size of the area 318, $A_{2,D2O}$ represents the size of the area 328.

The diagram 300 includes a chart 330, which is a superimposition of the chart 310 and 320. Areas 336 and 338 represent the area changes for the first and the second pore system, respectively. In one experiment, the sizes of the areas $A_{1,water}$, $A_{1,D2O}$, $A_{2,water}$, $A_{2,D2O}$ are calculated to be 10, 5, 1, and 0.9, respectively. The units of the areas can be either ml (for volume) or p.u. (for porosity). Accordingly, the pore connectivity factor is 0.2. While FIG. 3 uses the T1 relaxation time distribution curve as example, similar calculation can be performed based on the T2 relaxation time to determine pore connectivity factor.

Returning to FIG. 2, at 212, permeability is calculated with an input of the pore connectivity factor by Equation (2). In addition, if a porous media sample has more than two pore systems, a T1 or T2 cutoff value can be used to determine the BVM and BVI for the porous media sample. Accordingly, Equation (2) can also be used to determine the permeability of the porous media sample having more than two pore systems.

The permeability is one of petrophysical properties of the rocks in the reservoir where the porous media sample is collected, and can be used for estimating and forecasting the hydrocarbon productivity of the reservoir. Therefore, using the approach described in this disclosure can provide accurate permeability information, and thus improve the accuracy of reservoir estimation and production forecast. In addition, using the approach described in this disclosure to accurately assess the permeability will assist in developing Enhanced Oil Recovery (EOR) and Improved Oil Recovery (IOR) methods of the reservoir.

Figure 4:
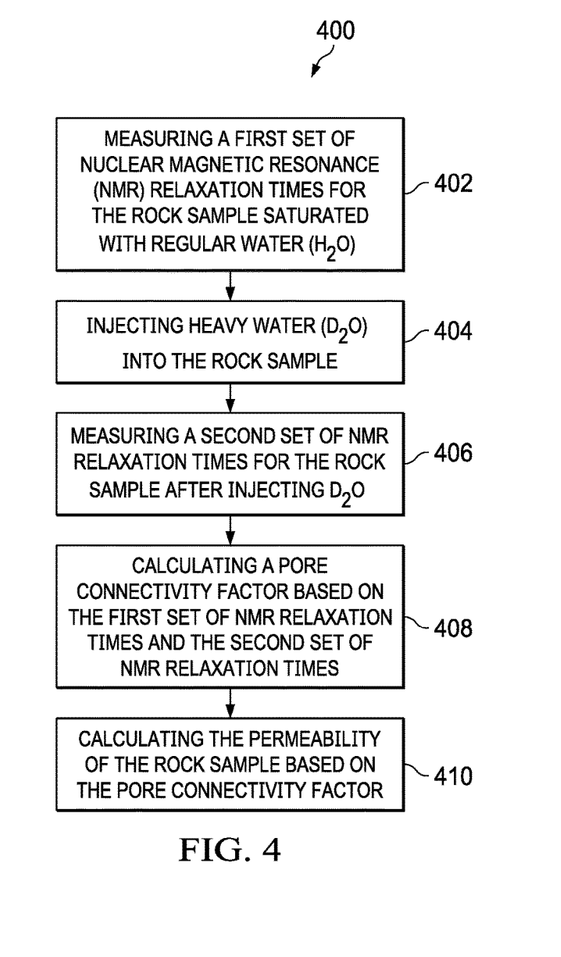
FIG. 4 illustrates an example permeability determination method, according to an implementation.

FIG. 4 illustrates an example permeability determination method 400, according to an implementation. For clarity of presentation, the description that follows generally describes method 400 in the context of FIGS. 1-3 and 5-6. However, it will be understood that method 400 may be performed, for example, by any other suitable system, environment, software, and hardware, or a combination of systems, environments, software, and hardware, as appropriate. In some cases, the method 400 can be executed on a computer cluster, super computers, or any other computing device or collection of computing devices. In some implementations, various steps of method 400 can be run in parallel, in combination, in loops, or in any order.

At 402, a first set of Nuclear Magnetic Resonance (NMR) relaxation times is measured for the rock sample saturated with regular water ($H_2O$). At 404, heavy water ($D_2O$) is injected into the rock sample. At 406, a second set of NMR relaxation times is measured for the rock sample after injecting $D_2O$. At 408, a pore connectivity factor is calculated based on the first set of NMR relaxation times and the second set of NMR relaxation times. At 410, a permeability of the rock sample is calculated based on the pore connectivity factor.

Figure 5:
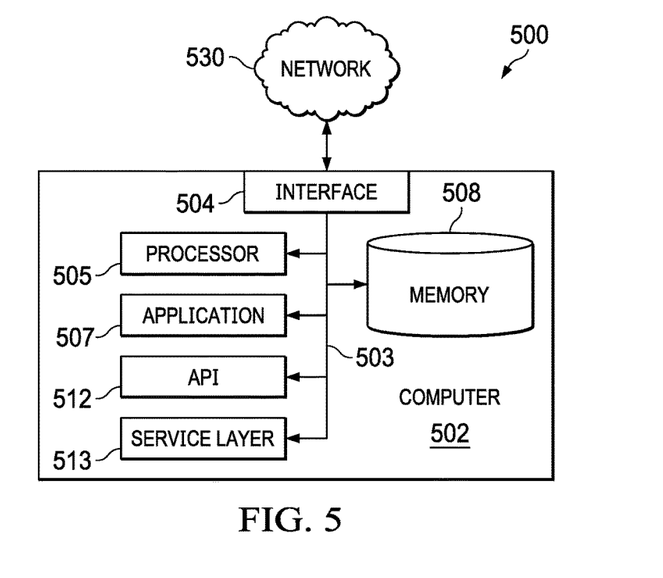
FIG. 5 is a high level architecture block diagram of a permeability determination system, according to an implementation.

FIG. 5 is a high level architecture block diagram of a permeability analyzing system 500 that analyzes permeability based on the methods described in this disclosure, according to an implementation. At a high level, the illustrated system 500 includes a computer 502 coupled with a network 530.

The described illustration is only one possible implementation of the described subject matter and is not intended to limit the disclosure to the single described implementation. Those of ordinary skill in the art will appreciate the fact that the described components can be connected, combined, or used in alternative ways, consistent with this disclosure.

The network 530 facilitates communication between the computer 502 and other components, for example, components that obtain observed data for a location and transmit the observed data to the computer 502. The network 530 can be a wireless or a wireline network. The network 530 can also be a memory pipe, a hardware connection, or any internal or external communication paths between the components.

The computer 502 includes a computing system configured to perform the method as described in this disclosure. For example, the computer 502 can be used to implement the NMR controller 102 and the analyzer 120 illustrated in FIG. 1. In some cases, the algorithm of the method can be implemented in an executable computing code, for example, C/C++ executable codes. In some cases, the computer 502 can include a standalone LINUX system that runs batch applications. In some cases, the computer 502 can include mobile or personal computers.

The computer 502 may comprise a computer that includes an input device, such as a keypad, keyboard, touch screen, microphone, speech recognition device, other devices that can accept user information, or an output device that conveys information associated with the operation of the computer 502, including digital data, visual or audio information, or a GUI.

The computer 502 can serve as a client, network component, a server, a database, or other persistency, or any other component of the system 500. In some implementations, one or more components of the computer 502 may be configured to operate within a cloud-computing-based environment.

At a high level, the computer 502 is an electronic computing device operable to receive, transmit, process, store, or manage data and information associated with the system 500. According to some implementations, the computer 502 may also include, or be communicably coupled with, an application server, e-mail server, web server, caching server, streaming data server, business intelligence (BI) server, or other server.

The computer 502 can receive requests over network 530 from a client application (for example, executing on another computer 502) and respond to the received requests by processing said requests in an appropriate software application. In addition, requests may also be sent to the computer 502 from internal users (for example, from a command console), external or third parties, or other automated applications.

Each of the components of the computer 502 can communicate using a system bus 503. In some implementations, any or all the components of the computer 502, both hardware or software, may interface with each other or the interface 504, over the system bus 503, using an application programming interface (API) 512 or a service layer 513. The API 512 may include specifications for routines, data structures, and object classes. The API 512 may be either computer language-independent or -dependent and refer to a complete interface, a single function, or even a set of APIs. The service layer 513 provides software services to the computer 502 or the system 500. The functionality of the computer 502 may be accessible for all service consumers using this service layer. Software services, such as those provided by the service layer 513, provide reusable, defined business functionalities, through a defined interface. For example, the interface may be software written in JAVA, C++, or suitable language providing data in Extensible Markup Language (XML) format. While illustrated as an integrated component of the computer 502, alternative implementations may illustrate the API 512 or the service layer 513 as stand-alone components in relation to other components of the computer 502 or the system 500. Moreover, any or all parts of the API 512 or the service layer 513 may be implemented as sub-modules of another software module, enterprise application, or hardware module, without departing from the scope of this disclosure.

The computer 502 includes an interface 504. Although illustrated as a single interface 504 in FIG. 5, two or more interfaces 504 may be used according to particular needs, desires, or particular implementations of the computer 502 or system 500. The interface 504 is used by the computer 502 for communicating with other systems in a distributed environment—including within the system 500—connected to the network 530 (whether illustrated or not). Generally, the interface 504 comprises logic encoded in software or hardware in a suitable combination and operable to communicate with the network 530. More specifically, the interface 504 may comprise software supporting one or more communication protocols associated with communications such that the network 530 or interface's hardware is operable to communicate physical signals within and outside of the illustrated system 500.

The computer 502 includes a processor 505. Although illustrated as a single processor 505 in FIG. 5, two or more processors may be used according to particular needs, desires, or particular implementations of the computer 502 or the system 500. Generally, the processor 505 executes instructions and manipulates data to perform the operations of the computer 502. Specifically, the processor 505 executes the functionality required for processing geophysical data.

The computer 502 also includes a memory 508 that holds data for the computer 502 or other components of the system 500. Although illustrated as a single memory 508 in FIG. 5, two or more memories may be used according to particular needs, desires, or particular implementations of the computer 502 or the system 500. While memory 508 is illustrated as an integral component of the computer 502, in alternative implementations, memory 508 can be external to the computer 502 or the system 500.

The application 507 is an algorithmic software engine providing functionality according to particular needs, desires, or particular implementations of the computer 502 or the system 500, particularly with respect to functionality required for processing geophysical data. For example, application 507 can serve as one or more components or applications described in FIGS. 1-4 and 6. Further, although illustrated as a single application 507, the application 507 may be implemented as multiple applications 507, on the computer 502. In addition, although illustrated as integral to the computer 502, in alternative implementations, the application 507 can be external to the computer 502 or the system 500.

There may be any number of computers 502 associated with, or external to, the system 500 and communicating over network 530. Further, the terms "client," "user," and other appropriate terminology may be used interchangeably, as appropriate, without departing from the scope of this disclosure. Moreover, this disclosure contemplates that many users may use one computer 502, or that one user may use multiple computers 502.

Described implementations of the subject matter can include one or more features, alone or in combination.

For example, in a first implementation, a method for determining a permeability of a rock sample includes: measuring a first set of Nuclear Magnetic Resonance (NMR) relaxation times for the rock sample saturated with regular water ($H_2O$); injecting heavy water ($D_2O$) into the rock sample; measuring a second set of NMR relaxation times for the rock sample after injecting $D_2O$; calculating a pore connectivity factor based on the first set of NMR relaxation times and the second set of NMR relaxation times; and calculating the permeability of the rock sample based on the pore connectivity factor.

The foregoing and other implementations can each, optionally, include one or more of the following features, alone or in combination:

A first aspect, combinable with the general implementation, where the second set of NMR relaxation times is measured after displacement of the rock sample stops.

A second aspect, combinable with any of the previous or following aspects, wherein the rock sample includes a first pore system and a second pore system, and the pore connective factor is calculated based on a ratio between a first volume displacement of the first pore system and a second volume displacement of the second pore system.

A third aspect, combinable with any of the previous or following aspects, where the first set of NMR relaxation times includes a first NMR relaxation time and a second NMR relaxation time, the first NMR relaxation time corresponding to a measurement of the first pore system after the rock sample is saturated with regular water, the second NMR relaxation time corresponding to a measurement of the second pore system after the rock sample is saturated with regular water, and the second set of NMR relaxation times includes a third NMR relaxation time and a fourth NMR relaxation time, the third NMR relaxation time corresponding to a measurement of the first pore system after the rock sample is injected with heavy water, and the fourth NMR relaxation time corresponding to a measurement of the second pore system after the rock sample is injected with heavy water.

A fourth aspect, combinable with any of the previous or following aspects, where the first volume displacement of the first pore system and the second volume displacement of the second pore system are calculated based on distribution curves associated with the first NMR relaxation time, the second NMR relaxation time, the third NMR relaxation time, and the fourth NMR relaxation time.

A fifth aspect, combinable with any of the previous or following aspects, where the first NMR relaxation time, the second NMR relaxation time, the third NMR relaxation time, and the fourth NMR relaxation time are NMR T1 relaxation times.

A sixth aspect, combinable with any of the previous or following aspects, where the first NMR relaxation time, the second NMR relaxation time, the third NMR relaxation time, and the fourth NMR relaxation time are NMR T2 relaxation times.

A seventh aspect, combinable with any of the previous aspects, where the permeability is calculated based on equation:

$$k = \left(\frac{\phi}{C}\right)^m \cdot \left(\frac{p \cdot BVM}{BVI + (1-p) \cdot BVM}\right)^n$$

where k is permeability, $\phi$ is porosity, BVM is bulk volume movable, BVI is bulk volume irreducible, p is the pore connectivity factor, and C, m, n are constant values.

In a second implementation, a system includes a nuclear magnetic resonance (NMR) instrument configured to: measure a first set of Nuclear Magnetic Resonance (NMR) relaxation times for a rock sample saturated with regular water ($H_2O$); and measure a second set of NMR relaxation times for the rock sample after the rock sample is injected with heavy water ($D_2O$); and a computer system connected to the NMR instrument, where the computer system includes: at least one hardware processor; and a non-transitory computer-readable storage medium coupled to the at least one hardware processor and storing programming instructions for execution by the at least one hardware processor, wherein the programming instructions, when executed, cause the at least one hardware processor to perform operations includes: calculating a pore connectivity factor based on the first set of NMR relaxation times and the second set of NMR relaxation times; and calculating a permeability of the rock sample based on the pore connectivity factor.

The foregoing and other implementations can each, optionally, include one or more of the following features, alone or in combination:

A first aspect, combinable with the general implementation, where the second set of NMR relaxation times is measured after displacement of the rock sample stops.

A second aspect, combinable with any of the previous or following aspects, wherein the rock sample includes a first pore system and a second pore system, and the pore connective factor is calculated based on a ratio between a first volume displacement of the first pore system and a second volume displacement of the second pore system.

A third aspect, combinable with any of the previous or following aspects, where the first set of NMR relaxation times includes a first NMR relaxation time and a second NMR relaxation time, the first NMR relaxation time corresponding to a measurement of the first pore system after the rock sample is saturated with regular water, the second NMR relaxation time corresponding to a measurement of the second pore system after the rock sample is saturated with regular water, and the second set of NMR relaxation times includes a third NMR relaxation time and a fourth NMR relaxation time, the third NMR relaxation time corresponding to a measurement of the first pore system after the rock sample is injected with heavy water, and the fourth NMR relaxation time corresponding to a measurement of the second pore system after the rock sample is injected with heavy water.

A fourth aspect, combinable with any of the previous or following aspects, where the first volume displacement of the first pore system and the second volume displacement of the second pore system are calculated based on distribution curves associated with the first NMR relaxation time, the second NMR relaxation time, the third NMR relaxation time, and the fourth NMR relaxation time.

A fifth aspect, combinable with any of the previous or following aspects, where the first NMR relaxation time, the second NMR relaxation time, the third NMR relaxation time, and the fourth NMR relaxation time are NMR T1 relaxation times.

A sixth aspect, combinable with any of the previous or following aspects, where the first NMR relaxation time, the second NMR relaxation time, the third NMR relaxation time, and the fourth NMR relaxation time are NMR T2 relaxation times.

A seventh aspect, combinable with any of the previous aspects, where the permeability is calculated based on equation:

$$k = \left(\frac{\phi}{C}\right)^m \cdot \left(\frac{p \cdot BVM}{BVI + (1-p) \cdot BVM}\right)^n$$

where k is permeability, $\phi$ is porosity, BVM is bulk volume movable, BVI is bulk volume irreducible, p is the pore connectivity factor, and C, m, n are constant values.

In a third implementation, a non-transitory computer-readable medium storing instructions which, when executed, cause a computer system to perform operations comprising: obtaining a first set of Nuclear Magnetic Resonance (NMR) relaxation times for a rock sample saturated with regular water ($H_2O$); obtaining a second set of NMR relaxation times for the rock sample after the rock sample is injected with heavy water ($D_2O$); calculating a pore connectivity factor based on the first set of NMR relaxation times and the second set of NMR relaxation times; and calculating a permeability of the rock sample based on the pore connectivity factor.

The foregoing and other implementations can each, optionally, include one or more of the following features, alone or in combination:

A first aspect, combinable with any of the previous aspects, wherein the rock sample includes a first pore system and a second pore system, and the pore connective factor is calculated based on a ratio between a first volume displacement of the first pore system and a second volume displacement of the second pore system.

A second aspect, combinable with any of the previous or following aspects, where the first set of NMR relaxation times includes a first NMR relaxation time and a second NMR relaxation time, the first NMR relaxation time corresponding to a measurement of the first pore system after the rock sample is saturated with regular water, the second NMR relaxation time corresponding to a measurement of the second pore system after the rock sample is saturated with regular water, and the second set of NMR relaxation times includes a third NMR relaxation time and a fourth NMR relaxation time, the third NMR relaxation time corresponding to a measurement of the first pore system after the rock sample is injected with heavy water, and the fourth NMR relaxation time corresponding to a measurement of the second pore system after the rock sample is injected with heavy water.

A third aspect, combinable with any of the previous or following aspects, where the first volume displacement of the first pore system and the second volume displacement of the second pore system are calculated based on distribution curves associated with the first NMR relaxation time, the second NMR relaxation time, the third NMR relaxation time, and the fourth NMR relaxation time.

A fourth aspect, combinable with any of the previous or following aspects, where the first NMR relaxation time, the second NMR relaxation time, the third NMR relaxation time, and the fourth NMR relaxation time are NMR T1 relaxation times.

A fifth aspect, combinable with any of the previous or following aspects, where the first NMR relaxation time, the second NMR relaxation time, the third NMR relaxation time, and the fourth NMR relaxation time are NMR T2 relaxation times.

A six aspect, combinable with any of the previous aspects, where the permeability is calculated based on equation:

$$k = \left(\frac{\phi}{C}\right)^m \cdot \left(\frac{p \cdot BVM}{BVI + (1-p) \cdot BVM}\right)^n$$

where k is permeability, φ is porosity, BVM is bulk volume movable, BVI is bulk volume irreducible, p is the pore connectivity factor, and C, m, n are constant values.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Implementations of the subject matter described in this specification can be implemented as one or more computer programs, that is, one or more modules of computer program instructions encoded on a tangible, non-transitory computer-storage medium for execution by, or to control the operation of, data processing apparatus. Alternatively or in addition, the program instructions can be encoded on an artificially generated propagated signal, for example, a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of one or more of them.

The terms "data processing apparatus," "computer," or "electronic computer device" (or equivalent as understood by one of ordinary skill in the art) refer to data processing hardware and encompass all kinds of apparatus, devices, and machines for processing data, including by way of example, a programmable processor, a computer, or multiple processors or computers. The apparatus can also be, or further include, special purpose logic circuitry, for example, a central processing unit (CPU), a FPGA (field programmable gate array), or an ASIC (application-specific integrated circuit). In some implementations, the data processing apparatus or special purpose logic circuitry may be hardware-based or software-based. The apparatus can optionally include code that creates an execution environment for computer programs, for example, code that constitutes processor firmware, a protocol stack, a database management system, an operating system, or a combination of one or more of them. The present disclosure contemplates the use of data processing apparatuses with or without conventional operating systems, for example LINUX, UNIX, WINDOWS, MAC OS, ANDROID, or IOS.

A computer program, which may also be referred to or described as a program, software, a software application, a module, a software module, a script, or code can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, for example, one or more scripts stored in a markup language document, in a single file dedicated to the program in question, or in multiple coordinated files, for example, files that store one or more modules, sub-programs, or portions of code. A computer program can be deployed to be executed on one computer or on multiple computers that are located at one site or distributed across multiple sites and interconnected by a communication network. While portions of the programs illustrated in the various figures are shown as individual modules that implement the various features and functionality through various objects, methods, or other processes, the programs may instead include a number of sub-modules, third-party services, components, or libraries. Conversely, the features and functionality of various components can be combined into single components, as appropriate.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, for example, a CPU, an FPGA, or an ASIC.

Computers suitable for the execution of a computer program can be based on general or special purpose microprocessors, both, or any other kind of CPU. Generally, a CPU will receive instructions and data from a read-only memory (ROM) or a random access memory (RAM) or both. The essential elements of a computer are a CPU for performing or executing instructions and one or more memory devices for storing instructions and data. Generally, a computer will also include, or be operatively coupled to, receive data from or transfer data to, or both, one or more mass storage devices for storing data, for example, magnetic, magneto-optical disks, or optical disks. However, a computer need not have such devices. Moreover, a computer can be embedded in another device, for example, a mobile telephone, a personal digital assistant (PDA), a mobile audio or video player, a game console, a global positioning system (GPS) receiver, or a portable storage device, for example, a universal serial bus (USB) flash drive, to name just a few.

Computer-readable media (transitory or non-transitory, as appropriate) suitable for storing computer program instructions and data include all forms of non-volatile memory, media and memory devices, including by way of example semiconductor memory devices, for example, erasable programmable read-only memory (EPROM), electrically erasable programmable read-only memory (EEPROM), and flash memory devices; magnetic disks, for example, internal hard disks or removable disks; magneto-optical disks; and CD-ROM, DVD+/−R, DVD-RAM, and DVD-ROM disks. The memory may store various objects or data, including caches, classes, frameworks, applications, backup data, jobs, web pages, web page templates, database tables, repositories storing business or dynamic information, and any other appropriate information including any parameters, variables, algorithms, instructions, rules, constraints, or references. Additionally, the memory may include any other appropriate data, such as logs, policies, security or access data, or reporting files. The processor and the memory can be supplemented by, or incorporated in, special purpose logic circuitry.

To provide for interaction with a user, implementations of the subject matter described in this specification can be implemented on a computer having a display device, for example, a CRT (cathode ray tube), LCD (liquid crystal display), LED (Light Emitting Diode), or plasma monitor, for displaying information to the user and a keyboard and a pointing device, for example, a mouse, trackball, or trackpad by which the user can provide input to the computer. Input may also be provided to the computer using a touchscreen, such as a tablet computer surface with pressure sensitivity or a multi-touch screen using capacitive or electric sensing. Other kinds of devices can be used to provide for interaction with a user as well; for example, feedback provided to the user can be any form of sensory feedback, for example, visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

The term "graphical user interface," or "GUI," may be used in the singular or the plural to describe one or more graphical user interfaces and each of the displays of a particular graphical user interface. Therefore, a GUI may represent any graphical user interface, including but not limited to, a web browser, a touch screen, or a command line interface (CLI) that processes information and efficiently presents the information results to the user. In general, a GUI may include a plurality of user interface (UI) elements, some or all associated with a web browser, such as interactive fields, pull-down lists, and buttons operable by the business suite user. These UI elements may be related to or represent the functions of the web browser.

Implementations of the subject matter described in this specification can be implemented in a computing system that includes a back-end component, for example, as a data server, or that includes a middleware component, for example, an application server, or that includes a front-end component, for example, a client computer having a graphical user interface or a Web browser through which a user can interact with an implementation of the subject matter described in this specification, or any combination of one or more such back-end, middleware, or front-end components. The components of the system can be interconnected by any form or medium of wireline or wireless digital data communication, for example, a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) using, for example, 802.11 a/b/g/n or 802.20, and all or a portion of the Internet. The network may communicate with, for example, Internet Protocol (IP) packets, Frame Relay frames, Asynchronous Transfer Mode (ATM) cells, voice, video, data, or other suitable information between network addresses.

The computing system can include clients and servers. A client and server are generally remote from each other and typically interact through a communication network. The relationship of client and server arises by virtue of computer programs running on the respective computers and having a client-server relationship to each other.

In some implementations, any or all of the components of the computing system, both hardware or software, may interface with each other or the interface using an application programming interface (API) or a service layer. The API may include specifications for routines, data structures, and object classes. The API may be either computer language independent or dependent and refer to a complete interface, a single function, or even a set of APIs. The service layer provides software services to the computing system. The functionality of the various components of the computing system may be accessible for all service consumers via this service layer. Software services provide reusable, defined business functionalities through a defined interface. For example, the interface may be software written in JAVA, C++, or other suitable language providing data in extensible markup language (XML) format or other suitable format. The API or service layer may be an integral or a stand-alone component in relation to other components of the computing system. Moreover, any or all parts of the service layer may be implemented as child or sub-modules of another software module, enterprise application, or hardware module without departing from the scope of this disclosure.

While this specification contains many specific implementation details, these should not be construed as limitations on the scope of any disclosure or on the scope of what may be claimed, but rather as descriptions of features that may be specific to particular implementations of particular disclosures. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described as acting in certain combinations and even initially claimed as such, one or more features from a claimed combination can in some cases be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking and parallel processing may be advantageous.

Moreover, the separation or integration of various system modules and components in the implementations described previously should not be understood as requiring such separation or integration in all implementations, and it should be understood that the described program components and systems can generally be integrated together in a single software product or packaged into multiple software products.

Accordingly, the previous description of example implementations does not define or constrain this disclosure. Other changes, substitutions, and alterations are also possible without departing from the spirit and scope of this disclosure.

What is claimed is:

1. A method for determining a permeability of a rock sample, comprising:
    measuring a first set of Nuclear Magnetic Resonance (NMR) relaxation times for the rock sample saturated with regular water ($H_2O$);
    injecting heavy water ($D_2O$) into the rock sample;
    measuring a second set of NMR relaxation times for the rock sample after injecting $D_2O$;
    calculating a pore connectivity factor based on the first set of NMR relaxation times and the second set of NMR relaxation times; and
    calculating the permeability of the rock sample based on the pore connectivity factor.

2. The method of claim 1, wherein the second set of NMR relaxation times is measured after displacement of the rock sample stops.

3. The method of claim 1, wherein the rock sample includes a first pore system and a second pore system, and the pore connective factor is calculated based on a ratio between a first volume displacement of the first pore system and a second volume displacement of the second pore system.

4. The method of claim 3, wherein the first set of NMR relaxation times includes a first NMR relaxation time and a second NMR relaxation time, the first NMR relaxation time corresponding to a measurement of the first pore system after the rock sample is saturated with regular water, the second NMR relaxation time corresponding to a measurement of the second pore system after the rock sample is saturated with regular water, and the second set of NMR relaxation times includes a third NMR relaxation time and a fourth NMR relaxation time, the third NMR relaxation time corresponding to a measurement of the first pore system after the rock sample is injected with heavy water, and the fourth NMR relaxation time corresponding to a measurement of the second pore system after the rock sample is injected with heavy water.

5. The method of claim 4, wherein the first volume displacement of the first pore system and the second volume displacement of the second pore system are calculated based on distribution curves associated with the first NMR relaxation time, the second NMR relaxation time, the third NMR relaxation time, and the fourth NMR relaxation time.

6. The method of claim 4, wherein the first NMR relaxation time, the second NMR relaxation time, the third NMR relaxation time, and the fourth NMR relaxation time are NMR T1 relaxation times.

7. The method of claim 4, wherein the first NMR relaxation time, the second NMR relaxation time, the third NMR relaxation time, and the fourth NMR relaxation time are NMR T2 relaxation times.

8. The method of claim 1, wherein the permeability is calculated based on equation:

$$k = \left(\frac{\phi}{C}\right)^m \cdot \left(\frac{p \cdot BVM}{BVI + (1-p) \cdot BVM}\right)^n$$

where k is permeability, $\phi$ is porosity, BVM is bulk volume movable, BVI is bulk volume irreducible, p is the pore connectivity factor, and C, m, n are constant values.

* * * * *